(12) United States Patent
Bednarz et al.

(10) Patent No.: US 8,575,362 B2
(45) Date of Patent: Nov. 5, 2013

(54) METHODS OF PREPARING 4-PHENYL-6-(2,2,2-TRIFLUORO-1-PHENYLETHOXY) PYRIMIDINE-BASED COMPOUNDS

(75) Inventors: Mark S. Bednarz, Yardley, PA (US); Hugh Alfred Burgoon, Jr., Hamilton, NJ (US); Shinya Iimura, Lawrenceville, NJ (US); Ramanaiah C. Kanamarlapudi, Bridgewater, NJ (US); Qiuling Song, Newark, DE (US); Wenxue Wu, Princeton Junction, NJ (US); Jie Yan, Plainsboro, NJ (US); Haiming Zhang, Pennington, NJ (US)

(73) Assignee: Lexicon Pharmaceuticals, Inc., The Woodlands, TX (US)

( * ) Notice: Subject to any disclaimer, the term of this patent is extended or adjusted under 35 U.S.C. 154(b) by 0 days.

(21) Appl. No.: 13/160,678

(22) Filed: Jun. 15, 2011

(65) Prior Publication Data
US 2011/0301349 A1 Dec. 8, 2011

Related U.S. Application Data

(60) Continuation of application No. 12/732,311, filed on Mar. 26, 2010, now Pat. No. 7,968,729, which is a division of application No. 12/196,341, filed on Aug. 22, 2008, now abandoned.

(60) Provisional application No. 60/957,744, filed on Aug. 24, 2007.

(51) Int. Cl.
C07D 231/12 (2006.01)

(52) U.S. Cl.
USPC ............... 548/374.1; 548/375.1; 548/377.1; 548/356.1

(58) Field of Classification Search
USPC ............... 548/374.1, 375.1, 377.1, 356.1
See application file for complete search history.

(56) References Cited

U.S. PATENT DOCUMENTS

| | | | |
|---|---|---|---|
| 4,866,181 A | 9/1989 | Brown | |
| 4,916,074 A | 4/1990 | Yoshida | |
| 5,233,111 A | 8/1993 | Notte | |
| 5,859,020 A | 1/1999 | Preuss | |
| 6,916,933 B2 | 7/2005 | Kaplan | |
| 7,553,840 B2 | 6/2009 | Devasagayaraj | |
| 7,709,493 B2 | 5/2010 | Devasagayaraj | |
| 7,723,345 B2 | 5/2010 | Devasagayaraj | |
| 7,855,291 B2 | 12/2010 | Burgoon | |
| 7,968,559 B2 | 6/2011 | Devasagayaraj | |
| 8,193,204 B2 * | 6/2012 | Bednarz et al. | 514/272 |
| 2003/0144541 A1 | 7/2003 | Jacquot | |
| 2005/0096353 A1 | 5/2005 | Ackermann | |
| 2005/0282900 A1 | 12/2005 | Kawaguchi | |
| 2006/0128956 A1 | 6/2006 | Hocek | |
| 2006/0148862 A1 | 7/2006 | Clary | |
| 2009/0088447 A1 | 4/2009 | Bednarz | |

FOREIGN PATENT DOCUMENTS

| | | |
|---|---|---|
| WO | WO 03/104189 | 12/2003 |
| WO | WO 03/104200 | 12/2003 |

OTHER PUBLICATIONS

Dondoni, A., et al., *Organic Let.* 6(17):2929-2932 (2004).
Firooznia et al., *Tetrahedron Lett.*, 49:213-216 (1999).
Hutton, C.A. and Skaff, O. *Tetrahedron Let.* 44(26):4895-4898 (2003).
Kuijpers, B.H.M., et al., *Organic Let.* 6(18):3123-3126 (2004).
Moussebois, C., et al., *Helv. Chimica Acta* 60(1):237-242 (1977).
Peyman, A., et al., *Angew. Chemie* 39(16):2874-2877 (2000).
Shi, Z. et al., *J. Med. Chem.* 51(13):3684-3687 (2008).
Yoburn, J.C. and Van Vranken, D.L., *Organic Let.* 5(16):2817-2820 (2003).
International Search Report issued for corresponding international patent application PCT/US2008/073950, Dec. 16, 2008.

* cited by examiner

*Primary Examiner* — Venkataraman Balasubramanian
(74) *Attorney, Agent, or Firm* — Max Bachrach

(57) ABSTRACT

Methods useful for preparing compounds of formula I:

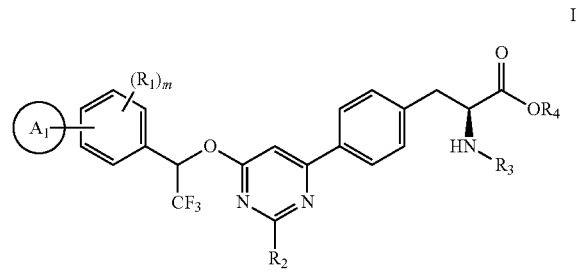

and salts thereof are disclosed. Also disclosed are intermediates useful in the preparation of such compounds.

9 Claims, 3 Drawing Sheets

METHODS OF PREPARING 4-PHENYL-6-(2,2,2-TRIFLUORO-1-PHENYLETHOXY) PYRIMIDINE-BASED COMPOUNDS

This application is a continuation of U.S. application Ser. No. 12/732,311, filed Mar. 26, 2010, which is a divisional of U.S. application Ser. No. 12/196,341, filed Aug. 22, 2008, which claims priority to U.S. provisional application No. 60/957,744, filed Aug. 24, 2007, the entireties of which are incorporated herein by reference.

1. FIELD OF THE INVENTION

This invention relates to methods of making 4-phenyl-6-(2,2,2-trifluoro-1-phenylethoxy)pyrimidine-based compounds.

2. BACKGROUND

Certain 4-phenyl-6-(2,2,2-trifluoro-1-phenylethoxy)pyrimidine-based compounds are inhibitors of the enzyme tryptophan hydroxylase (TPH), which catalyzes the rate limiting step of serotonin's biosynthesis. See U.S. patent application Ser. Nos. 11/638,677 and 60/874,596, both filed Dec. 12, 2006. It is believed that these compounds may be used to treat a wide range of diseases and disorders associated with the serotonergic system. Id. Consequently, efficient methods of their manufacture are desired.

3. SUMMARY OF THE INVENTION

This invention encompasses methods of preparing compounds of formula I:

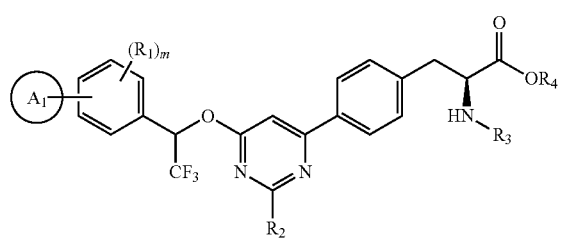

I and salts thereof, the various substituents of which are defined herein. When administered to mammals, preferred compounds of this formula inhibit TPH (e.g., TPH1), and may be useful in the treatment of various diseases and disorders.

This invention also encompasses intermediates that are useful in the synthesis of compounds of formula I.

4. BRIEF DESCRIPTION OF THE FIGURES

5. DETAILED DESCRIPTION

Figure 1:
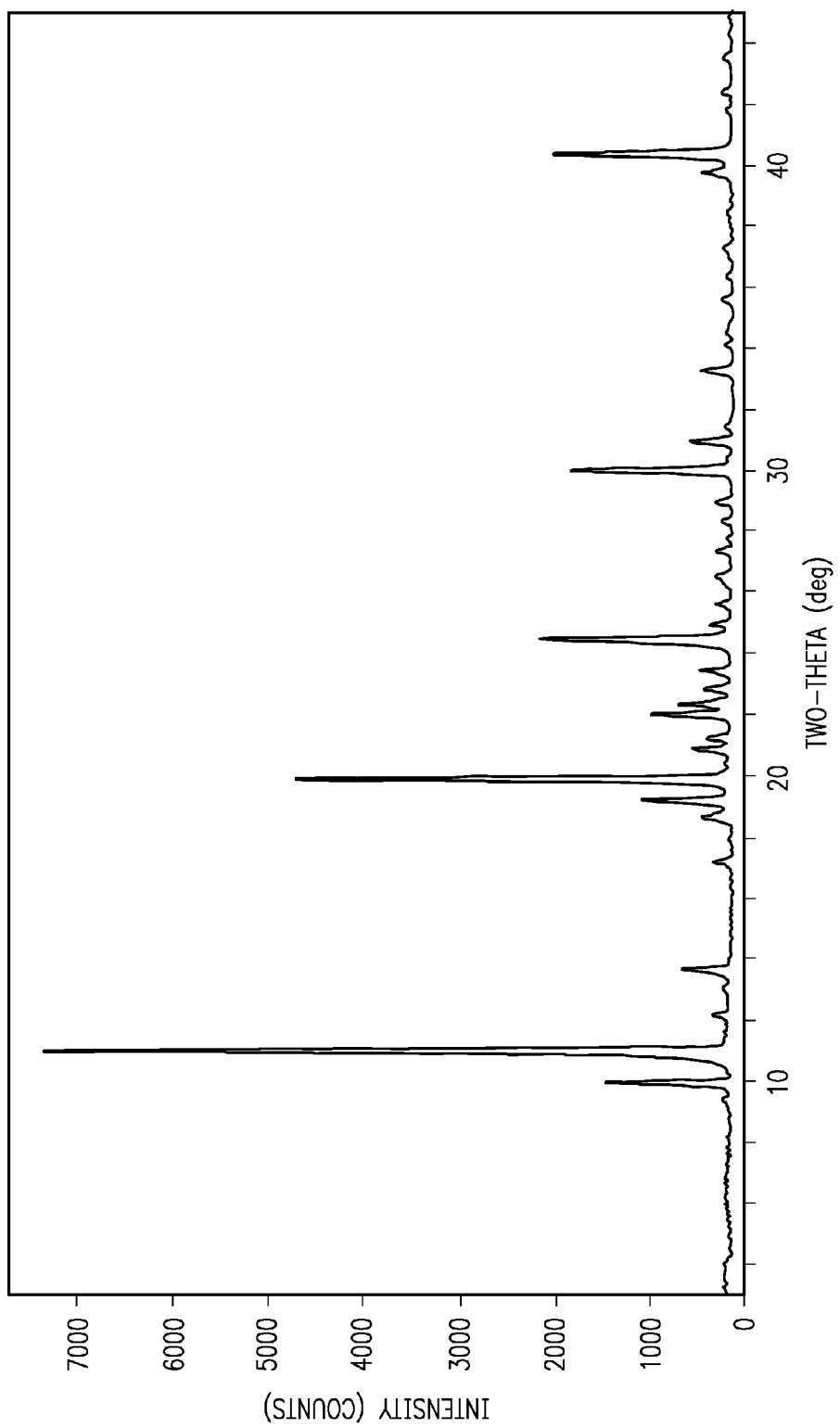
FIG. 1 is an X-ray diffraction pattern of a crystalline solid form of (R)-1-(4-chloro-2-(3-methyl-1H-pyrazol-1-yl)phenyl)-2,2,2-trifluoroethanol. The pattern was obtained using a Rigaku MiniFlex diffractometer (Cu (1.54060 Å) radiation).

This invention is based on the discovery of novel methods of preparing compounds of formula I and intermediates useful therein. When administered to mammals, preferred compounds of formula I inhibit TPH, and may be used in the treatment of a variety of diseases and disorders. See generally, U.S. patent application Ser. Nos. 11/638,677 and 60/874,596, both filed Dec. 12, 2006.

5.1. DEFINITIONS

Unless otherwise indicated, the term "alkenyl" means a straight chain, branched and/or cyclic hydrocarbon having from 2 to 20 (e.g., 2 to 10 or 2 to 6) carbon atoms, and including at least one carbon-carbon double bond. Representative alkenyl moieties include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl and 3-decenyl.

Unless otherwise indicated, the term "alkoxy" means an —O-alkyl group. Examples of alkoxy groups include —OCH$_3$, —OCH$_2$CH$_3$, —O(CH$_2$)$_2$CH$_3$, —O(CH$_2$)$_3$CH$_3$, —O(CH$_2$)$_4$CH$_3$, —O(cyclopenyl) and —O(CH$_2$)$_5$CH$_3$. The term "lower alkoxy" refers to —O-(lower alkyl).

Unless otherwise indicated, the term "alkyl" means a straight chain, branched and/or cyclic ("cycloalkyl") hydrocarbon having from 1 to 20 (e.g., 1 to 10 or 1 to 4) carbon atoms. Alkyl moieties having from 1 to 4 carbons are referred to as "lower alkyl." Examples of alkyl groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl and dodecyl. Cycloalkyl moieties may be monocyclic or multicyclic, and examples include cyclopropyl, cyclobutyl, cyclopentyl, cyclohexyl, and adamantyl. Additional examples of alkyl moieties have linear, branched and/or cyclic portions (e.g., 1-ethyl-4-methyl-cyclohexyl). The term "alkyl" includes saturated hydrocarbons as well as alkenyl and alkynyl moieties.

Unless otherwise indicated, the term "alkylaryl" or "alkyl-aryl" means an alkyl moiety bound to an aryl moiety.

Unless otherwise indicated, the term "alkylheteroaryl" or "alkyl-heteroaryl" means an alkyl moiety bound to a heteroaryl moiety.

Unless otherwise indicated, the term "alkylheterocycle" or "alkyl-heterocycle" means an alkyl moiety bound to a heterocycle moiety.

Unless otherwise indicated, the term "alkynyl" means a straight chain, branched or cyclic hydrocarbon having from 2 to 20 (e.g., 2 to 20 or 2 to 6) carbon atoms, and including at least one carbon-carbon triple bond. Representative alkynyl moieties include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl and 9-decynyl.

Unless otherwise indicated, the term "aryl" means an aromatic ring or an aromatic or partially aromatic ring system composed of carbon and hydrogen atoms. An aryl moiety may comprise multiple rings bound or fused together. Examples of aryl moieties include anthracenyl, azulenyl, biphenyl, fluorenyl, indan, indenyl, naphthyl, phenanthrenyl, phenyl, 1,2,3,4-tetrahydro-naphthalene, and tolyl.

Unless otherwise indicated, the term "arylalkyl" or "aryl-alkyl" means an aryl moiety bound to an alkyl moiety.

Unless otherwise indicated, the terms "biohydrolyzable amide," "biohydrolyzable ester," "biohydrolyzable carbamate," "biohydrolyzable carbonate," "biohydrolyzable ureido" and "biohydrolyzable phosphate" mean an amide, ester, carbamate, carbonate, ureido, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include lower alkyl esters, alkoxyacyloxy esters, alkyl acylamino alkyl esters, and choline esters. Examples of biohydrolyzable amides include lower alkyl amides, α-amino acid amides, alkoxyacyl amides, and alkylaminoalkyl-carbonyl amides. Examples of biohydrolyzable carbamates include lower alkylamines, substituted ethylenediamines, aminoacids, hydroxyalkylamines, heterocyclic and heteroaromatic amines, and polyether amines.

Unless otherwise indicated, the terms "halogen" and "halo" encompass fluorine, chlorine, bromine, and iodine.

Unless otherwise indicated, the term "heteroalkyl" refers to an alkyl moiety (e.g., linear, branched or cyclic) in which at least one of its carbon atoms has been replaced with a heteroatom (e.g., N, O or S).

Unless otherwise indicated, the term "heteroaryl" means an aryl moiety wherein at least one of its carbon atoms has been replaced with a heteroatom (e.g., N, O or S). Examples include acridinyl, benzimidazolyl, benzofuranyl, benzoisothiazolyl, benzoisoxazolyl, benzoquinazolinyl, benzothiazolyl, benzoxazolyl, furyl, imidazolyl, indolyl, isothiazolyl, isoxazolyl, oxadiazolyl, oxazolyl, phthalazinyl, pyrazinyl, pyrazolyl, pyridazinyl, pyridyl, pyrimidinyl, pyrimidyl, pyrrolyl, quinazolinyl, quinolinyl, tetrazolyl, thiazolyl, and triazinyl.

Unless otherwise indicated, the term "heteroarylalkyl" or "heteroaryl-alkyl" means a heteroaryl moiety bound to an alkyl moiety.

Unless otherwise indicated, the term "heterocycle" refers to an aromatic, partially aromatic or non-aromatic monocyclic or polycyclic ring or ring system comprised of carbon, hydrogen and at least one heteroatom (e.g., N, O or S). A heterocycle may comprise multiple (i.e., two or more) rings fused or bound together. Heterocycles include heteroaryls. Particular heterocycles are 5- to 13-membered heterocycles containing 1 to 4 heteroatoms selected from nitrogen, oxygen, and sulphur. Others are 5- to 10-membered heterocycles containing 1 to 4 heteroatoms selected from nitrogen, oxygen, and sulphur. Examples of heterocycles include benzo[1,3]dioxolyl, 2,3-dihydro-benzo[1,4]dioxinyl, cinnolinyl, furanyl, hydantoinyl, morpholinyl, oxetanyl, oxiranyl, piperazinyl, piperidinyl, pyrrolidinonyl, pyrrolidinyl, tetrahydrofuranyl, tetrahydropyranyl, tetrahydropyridinyl, tetrahydropyrimidinyl, tetrahydrothiophenyl, tetrahydrothiopyranyl and valerolactamyl.

Unless otherwise indicated, the term "heterocyclealkyl" or "heterocycle-alkyl" refers to a heterocycle moiety bound to an alkyl moiety.

Unless otherwise indicated, the term "heterocycloalkyl" refers to a non-aromatic heterocycle.

Unless otherwise indicated, the term "heterocycloalkylalkyl" or "heterocycloalkyl-alkyl" refers to a heterocycloalkyl moiety bound to an alkyl moiety.

Unless otherwise indicated, the term "prodrug" encompasses pharmaceutically acceptable esters, carbonates, thiocarbonates, N-acyl derivatives, N-acyloxyalkyl derivatives, quaternary derivatives of tertiary amines, N-Mannich bases, Schiff bases, amino-acid conjugates, phosphate esters, metal salts and sulfonate esters of compounds disclosed herein. Examples of prodrugs include compounds that comprise a biohydrolyzable moiety (e.g., a biohydrolyzable amide, biohydrolyzable carbamate, biohydrolyzable carbonate, biohydrolyzable ester, biohydrolyzable phosphate, or biohydrolyzable ureide analog). Prodrugs of compounds disclosed herein are readily envisioned and prepared by those of ordinary skill in the art. See, e.g., *Design of Prodrugs*, Bundgaard, A. Ed., Elseview, 1985; Bundgaard, hours., "Design and Application of Prodrugs," *A Textbook of Drug Design and Development*, Krosgaard-Larsen and hours. Bundgaard, Ed., 1991, Chapter 5, p. 113-191; and Bundgaard, hours., *Advanced Drug Delivery Review*, 1992, 8, 1-38.

Unless otherwise indicated, the term "protecting group" or "protective group," when used to refer to part of a molecule subjected to a chemical reaction, means a chemical moiety that is not reactive under the conditions of that chemical reaction, and which may be removed to provide a moiety that is reactive under those conditions. Protecting groups are well known in the art. See, e.g., Greene, T. W. and Wuts, P. G. M., *Protective Groups in Organic Synthesis* ($3^{rd}$ ed., John Wiley & Sons: 1999); Larock, R. C., *Comprehensive Organic Transformations* ($2^{nd}$ ed., John Wiley & Sons: 1999). Some examples include benzyl, diphenylmethyl, trityl, Cbz, Boc, Fmoc, methoxycarbonyl, ethoxycarbonyl, and pthalimido.

Unless otherwise indicated, the term "pseudohalogen" refers to a polyatomic anion that resembles a halide ion in its acid-base, substitution, and redox chemistry, generally has low basicity, and forms a free radical under atom transfer radical polymerization conditions. Examples of pseudohalogens include azide ions, cyanide, cyanate, thiocyanate, thiosulfate, sulfonates, and sulfonyl halides.

Unless otherwise indicated, the term "stereomerically enriched composition of" a compound refers to a mixture of the named compound and its stereoisomer(s) that contains more of the named compound than its stereoisomer(s). For example, a stereoisomerically enriched composition of (S)-butan-2-ol encompasses mixtures of (S)-butan-2-ol and (R)-butan-2-ol in ratios of, e.g., about 60/40, 70/30, 80/20, 90/10, 95/5, and 98/2.

Unless otherwise indicated, the term "stereoisomeric mixture" encompasses racemic mixtures as well as stereomerically enriched mixtures (e.g., R/S=30/70, 35/65, 40/60, 45/55, 55/45, 60/40, 65/35 and 70/30).

Unless otherwise indicated, the term "stereomerically pure" means a composition that comprises one stereoisomer of a compound and is substantially free of other stereoisomers of that compound. For example, a stereomerically pure composition of a compound having one stereocenter will be substantially free of the opposite stereoisomer of the compound. A stereomerically pure composition of a compound having two stereocenters will be substantially free of other diastereomers of the compound. A stereomerically pure composition of a compound that has multiple stereocenters, but which is drawn or named in such a way that the stereochemistries of less than all of its stereocenters are defined, is substantially free of the isomers of the compound that have different stereochemistries at the stereocenters for which stereochemistry is defined. For example, "stereomerically pure ((1R)-1,2-dichloropropyl)benzene" refers to ((1R)-1,2-dichloropropyl) benzene that is substantially free of ((1S)-1,2-dichloropropyl)benzene.

A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, greater than about 97% by weight of one stereoisomer of the compound and less than about 3% by weight of the other stereoisomers of the compound, or greater than about 99% by weight of one stereoisomer of the compound and less than about 1% by weight of the other stereoisomers of the compound.

Unless otherwise indicated, the term "substituted," when used to describe a chemical structure or moiety, refers to a derivative of that structure or moiety wherein one or more of its hydrogen atoms is substituted with an atom, chemical moiety or functional group such as alcohol, aldehyde, alkoxy, alkanoyloxy, alkoxycarbonyl, alkenyl, alkyl (e.g., methyl, ethyl, propyl, t-butyl), alkynyl, alkylcarbonyloxy(—OC(O) alkyl), amide (—C(O)NH-alkyl- or -alkylNHC(O)alkyl), amidinyl (—C(NH)NH-alkyl- or —C(NR)NH$_2$), amine (primary, secondary and tertiary such as alkylamino, arylamino, arylalkylamino), aroyl, aryl, aryloxy, azo, carbamoyl (—NHC(O)O-alkyl- or —OC(O)NH-alkyl), carbamyl (e.g., CONH$_2$, as well as CONH-alkyl, CONH-aryl, and CONH-arylalkyl), carbonyl, carboxyl, carboxylic acid, carboxylic acid anhydride, carboxylic acid chloride, cyano, ester, epoxide, ether (e.g., methoxy, ethoxy), guanidino, halo, haloalkyl (e.g., —CCl$_3$, —CF$_3$, —C(CF$_3$)$_3$), heteroalkyl, hemiacetal, imine (primary and secondary), isocyanate, isothiocyanate, ketone, nitrile, nitro, oxygen (i.e., to provide an oxo group), phosphodiester, sulfide, sulfonamido (e.g., SO$_2$NH$_2$), sulfone, sulfonyl (including alkylsulfonyl, arylsulfonyl and arylalkylsulfonyl), sulfoxide, thiol (e.g., sulfhydryl, thioether) and urea (—NHCONH-alkyl-).

Unless otherwise indicated, the phrase "greater than X," where X is a number, has the same meaning as "X or greater than X." Similarly, the phrase "greater than about X," where X is a number, has the same meaning as "about X or greater than about X."

Unless otherwise indicated, the phrase "less than X," where X is a number, has the same meaning as "X or less than X." Similarly, the phrase "less than about X," where X is a number, has the same meaning as "about X or less than about X."

Unless otherwise indicated, the phrase "between X and Y" encompasses values between X and Y as well as X and Y themselves. Similarly, the phrases "between about X and about Y" and "between about X and Y" both refer to values between about X and about Y, including about X and about Y.

Unless otherwise indicated, the term "include" has the same meaning as "include" and the term "includes" has the same meaning as "includes, but is not limited to." Similarly, the term "such as" has the same meaning as the term "such as, but not limited to."

Unless otherwise indicated, one or more adjectives immediately preceding a series of nouns is to be construed as applying to each of the nouns. For example, the phrase "optionally substituted alky, aryl, or heteroaryl" has the same meaning as "optionally substituted alky, optionally substituted aryl, or optionally substituted heteroaryl."

Unless otherwise indicated, a structure or name of a compound or genus of compounds encompasses all forms of that compound or genus of compounds, and all compositions comprising that compound or genus of compounds.

It should be noted that a chemical moiety that forms part of a larger compound may be described herein using a name commonly accorded it when it exists as a single molecule or a name commonly accorded its radical. For example, the terms "pyridine" and "pyridyl" are accorded the same meaning when used to describe a moiety attached to other chemical moieties. Thus, the two phrases "XOH, wherein X is pyridyl" and "XOH, wherein X is pyridine" are accorded the same meaning, and encompass the compounds pyridin-2-ol, pyridin-3-ol and pyridin-4-ol.

It should also be noted that if the stereochemistry of a structure or a portion of a structure is not indicated with, for example, bold or dashed lines, the structure or the portion of the structure is to be interpreted as encompassing all stereoisomers of it. Similarly, names of compounds having one or more chiral centers that do not specify the stereochemistry of those centers encompass pure stereoisomers and mixtures thereof. Moreover, any atom shown in a drawing with unsatisfied valences is assumed to be attached to enough hydrogen atoms to satisfy the valences. In addition, chemical bonds depicted with one solid line parallel to one dashed line encompass both single and double (e.g., aromatic) bonds, if valences permit.

5.2. METHODS OF SYNTHESIS

This invention encompasses methods of preparing compounds of formula I:

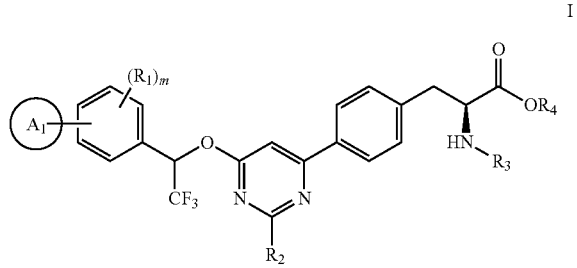

and salts (e.g., pharmaceutically acceptable salts) thereof, wherein: A$_1$ is optionally substituted heterocycle; each R$_1$ is independently amino, halogen, hydrogen, C(O)R$_A$, OR$_A$, NR$_B$R$_C$, S(O$_2$)R$_A$, or optionally substituted alkyl, alkyl-aryl or alkyl-heterocycle; R$_2$ is independently amino, halogen, hydrogen, C(O)R$_A$, OR$_A$, NR$_B$R$_C$, S(O$_2$)R$_A$, or optionally substituted alkyl, alkyl-aryl or alkyl-heterocycle; R$_3$ is hydrogen, C(O)R$_A$, C(O)OR$_A$, or optionally substituted alkyl, alkyl-aryl, alkyl-heterocycle, aryl, or heterocycle; R$_4$ is hydrogen or optionally substituted alkyl, alkyl-aryl, alkyl-heterocycle, aryl, or heterocycle; each R$_A$ is independently hydrogen or optionally substituted alkyl, alkyl-aryl or alkyl-heterocycle; each R$_B$ is independently hydrogen or optionally substituted alkyl, alkyl-aryl or alkyl-heterocycle; each R$_C$ is independently hydrogen or optionally substituted alkyl, alkyl-aryl or alkyl-heterocycle; and m is 1-4.

In certain embodiments of the invention, A$_1$ is aromatic; in others, it is not. In others, A$_1$ is optionally substituted with one or more of halogen or lower alkyl.

In some, the compound of formula I is of formula I(a):

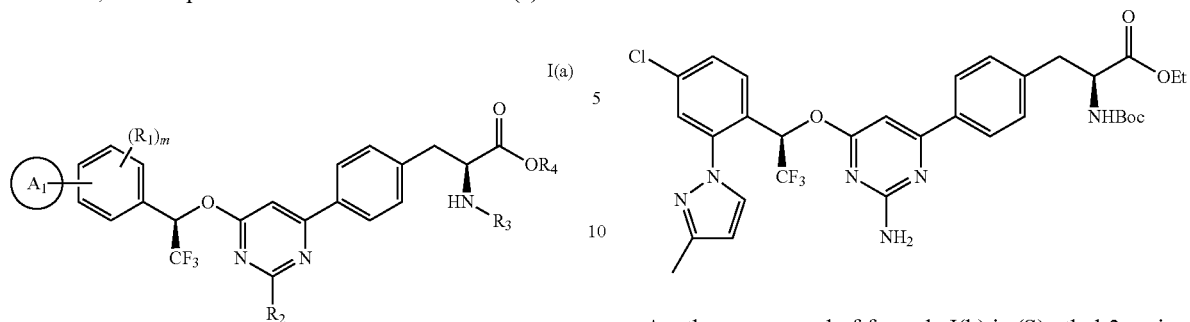

In particular embodiments, the compound of formula I(a) is formula I(b):

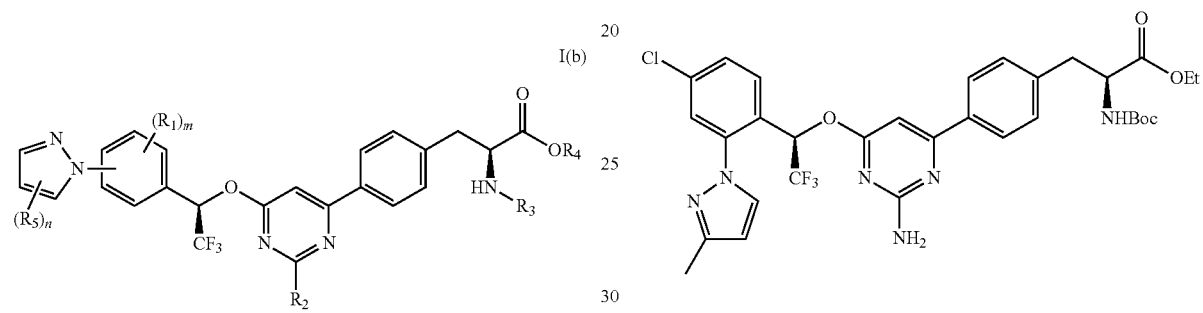

wherein: each $R_5$ is independently amino, halogen, hydrogen, $C(O)R_A$, $OR_A$, $NR_BR_C$, $S(O_2)R_A$, or optionally substituted alkyl, alkyl-aryl or alkyl-heterocycle; and n is 1-3.

In some embodiments, $R_1$ is hydrogen or halogen. In some, m is 1. In some, $R_2$ is hydrogen or amino. In some, $R_3$ is hydrogen or lower alkyl. In some, $R_3$ is $C(O)OR_A$ and $R_A$ is alkyl. In some, $R_4$ is hydrogen or lower alkyl. In some, $R_5$ is hydrogen or lower alkyl (e.g., methyl). In some, n is 1.

A particular compound of formula I(b) is (S)-3-(4-(2-amino-6-((R)-1-(4-chloro-2-(3-methyl-1H-pyrazol-1-yl)phenyl)-2,2,2-trifluoroethoxy)pyrimidin-4-yl)phenyl)-2-(tert-butoxycarbonylamino)propanoic acid:

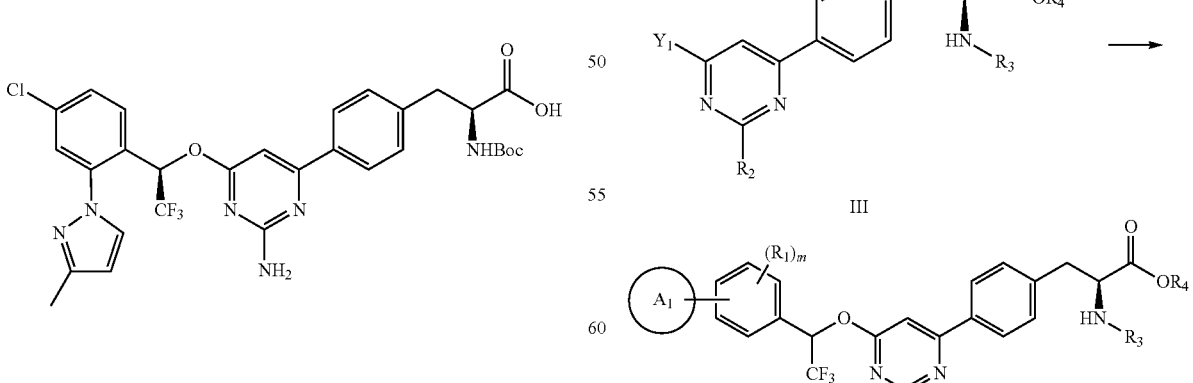

Another compound of formula I(b) is (S)-ethyl 3-(4-(2-amino-6-((R)-1-(4-chloro-2-(3-methyl-1H-pyrazol-1-yl)phenyl)-2,2,2-trifluoroethoxy)pyrimidin-4-yl)phenyl)-2-(tert-butoxycarbonylamino)propanoate:

Another compound of formula I(b) is (S)-ethyl 2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoate:

In one embodiment of the invention, the compound of formula I is prepared according to the general approach shown below in Scheme 1:

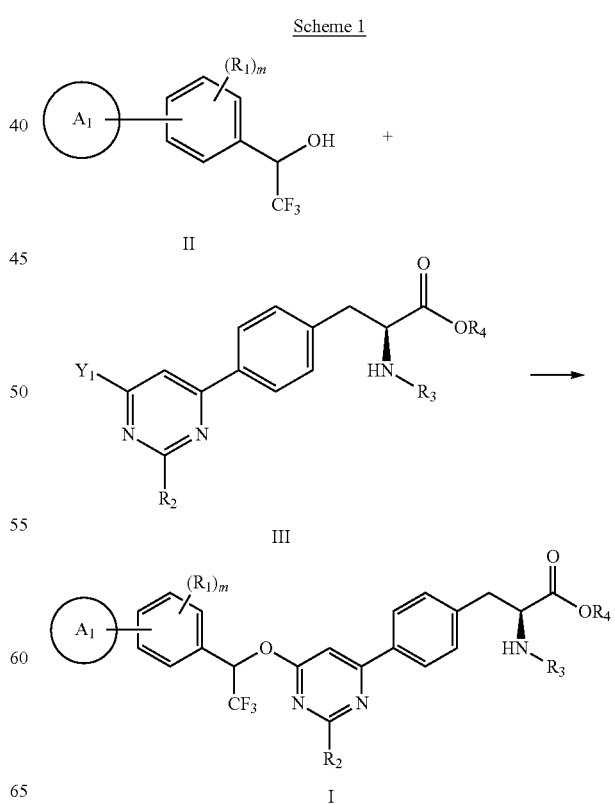

wherein Y₁ is halogen or pseudohalogen. Here, a compound of formula II is contacted with one of formula III under suitable reaction conditions. Such conditions include the use of a base (e.g., alkyllithium, alkylmagnesium, alkoxides, alkaline metal hydroxides, alkaline metal phosphates, and alkaline metal carbonates), a temperature of from about 50 to about 150° C., a reaction time of from about 10 to about 40 hours, and polar aprotic solvents. A particular base is cesium carbonate.

In certain embodiments, the compound of formula II is of formula II(a):

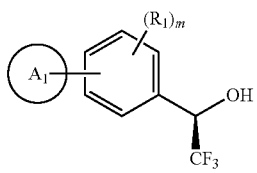

II(a)

In some such compounds, R₁ is chloro and m is 1. A particular compound is (R)-1-(4-chloro-2-(3-methyl-1H-pyrazol-1-yl)phenyl)-2,2,2-trifluoroethanol:

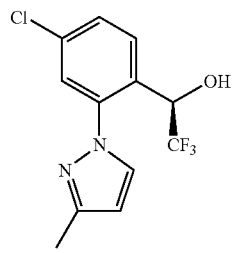 [SMILES: Cc1ccn(-c2cc(Cl)ccc2[C@@H](O)C(F)(F)F)n1]

A particular crystalline form of this compound has a melting point of about 120° C. as measured by differential scanning calorimetry (DSC) (onset temperature). In this context, the term "about" means±5.0° C. The form provides a X-ray powder diffraction (XRPD) pattern with peaks at one or more of about 9.9, 11.0, 19.2, 19.9, 24.4, 30.0, 31.0 and/or 40.4 degrees 2θ. In this context, the term "about" means±0.3 degrees. As those skilled in the art are well aware, the relative intensities of peaks in a X-ray diffraction pattern of a crystalline form can vary depending on how the sample is prepared and how the data is collected. With this in mind, an example of a XRPD pattern of this crystalline form is provided in FIG. 1.

Compounds of formula II can be prepared by reducing compounds of formula IV:

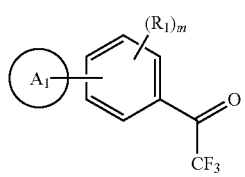

IV using methods generally known as Noyori hydrogenation and Noyori transfer hydrogenation. In a particular method, the reduction is achieved using a platinum group metal (e.g., iridium, ruthenium, rhodium) catalyst with a Noyori-type chiral ligand, such as (1R,2R)-(-)—N-(4-toluenesulfonyl)-1,2-diphenylethylenediamine.

A particular compound of formula IV is 1-(4-chloro-2-(3-methyl-1H-pyrazol-1-yl)phenyl)-2,2,2-trifluoroethanone:

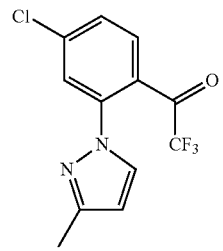 [SMILES: Cc1ccn(-c2cc(Cl)ccc2C(=O)C(F)(F)F)n1]

Figure 2:
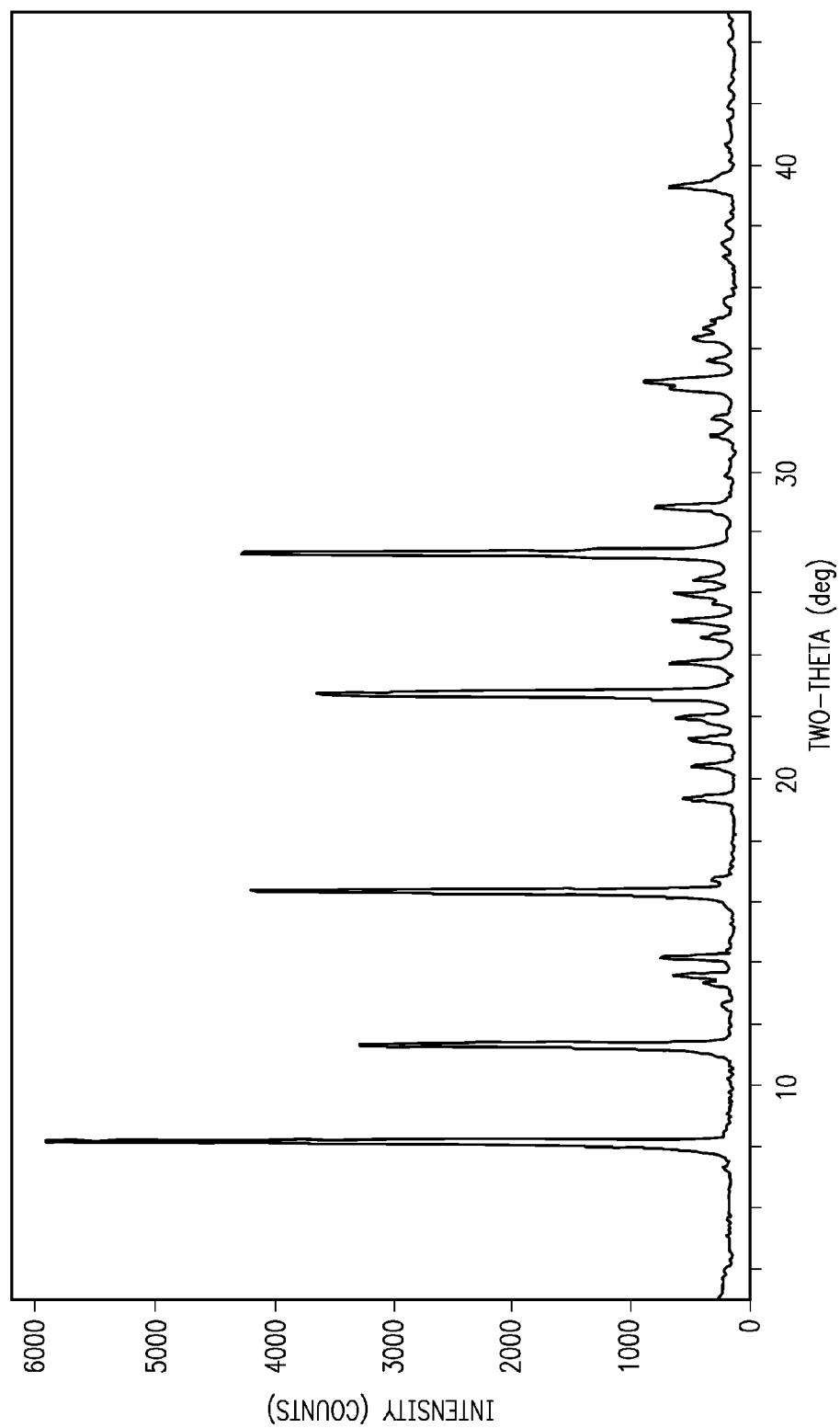
FIG. 2 is an X-ray diffraction pattern of a crystalline solid form of 1-(4-chloro-2-(3-methyl-1H-pyrazol-1-yl)phenyl)-2,2,2-trifluoroethanone. The pattern was obtained using a Rigaku MiniFlex diffractometer (Cu (1.54060 Å) radiation).

A particular crystalline form of this compound has a melting point of about 83° C. as measured by DSC (onset temperature). In this context, the term "about" means±5.0° C. The form provides a XRPD pattern with peaks at one or more of about 8.1, 11.3, 16.3, 22.7 and/or 27.3 degrees 2θ. In this context, the term "about" means±0.3 degrees. An example of a XRPD pattern of this crystalline form is provided in FIG. 2.

Compounds of formula IV can be prepared from compounds of formula V:

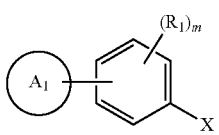

V wherein X is bromine or iodine. For example, a compound of formula V can be reacted with an alkyllithium or alkylmagnesium reagent to form the corresponding lithium or magnesium compound, which can then be reacted with ethyl 2,2,2-trifluoroacetate. Particular alkyl lithium reagents include n-butyllithium, sec-butyllithium, and t-butyllithium. Particular magnesium reagents include isopropyl magnesium chloride and tributylmagnesium chloride. Suitable reaction conditions include temperatures of from about -80 to about 40° C., reaction times of from about 10 minutes to about 10 hours, and aprotic solvents. Thus, the compound 1-(4-chloro-2-(3-methyl-1H-pyrazol-1-yl)phenyl)-2,2,2-trifluoroethanone can be prepared from 1-(2-bromo-5-chlorophenyl)-3-methyl-1H-pyrazole:

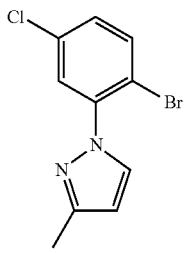

Figure 3:
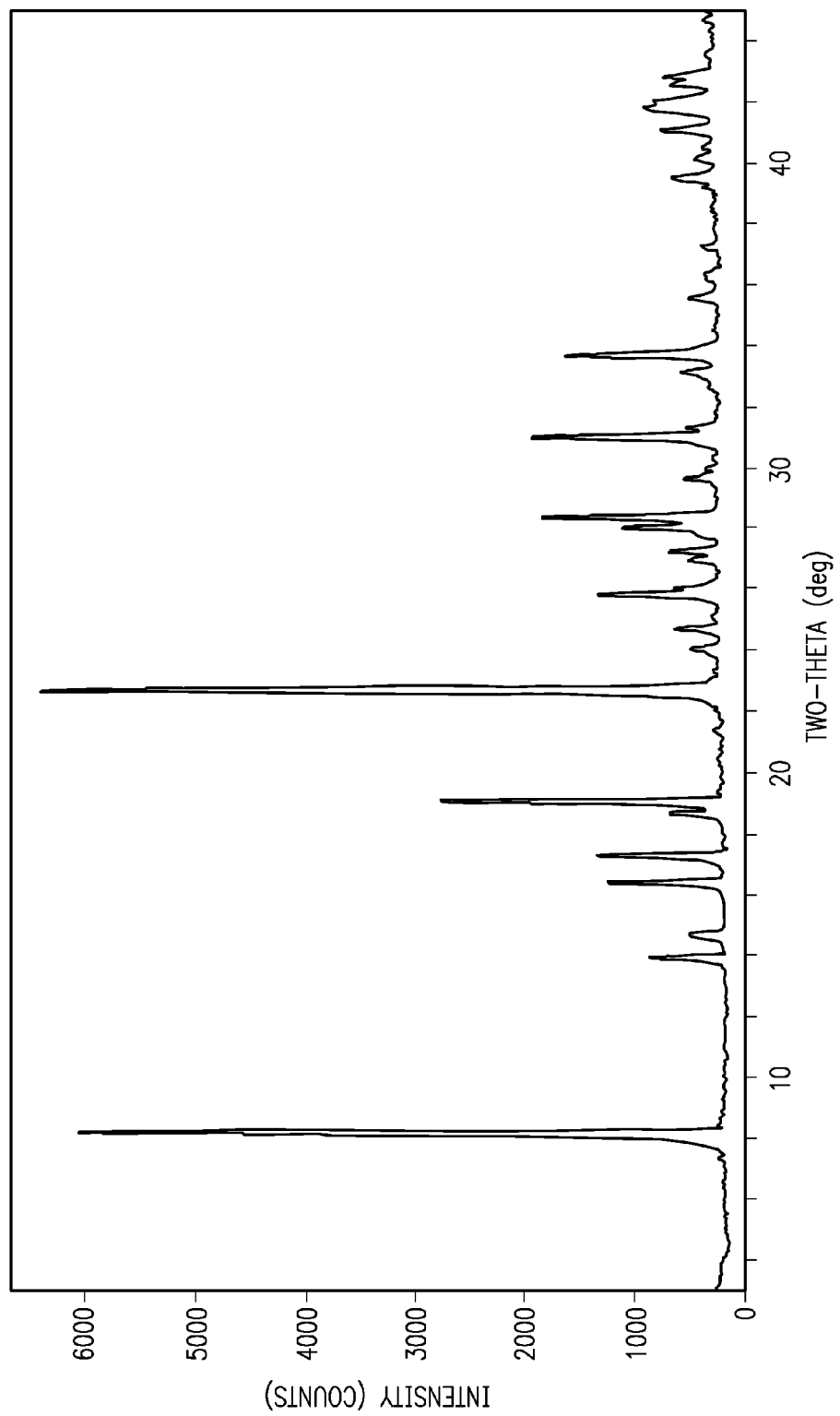
FIG. 3 is an X-ray diffraction pattern of a crystalline solid form of 1-(2-bromo-5-chlorophenyl)-3-methyl-1H-pyrazole. The pattern was obtained using a Rigaku MiniFlex diffractometer (Cu (1.54060 Å) radiation).

A particular crystalline form of this compound has a melting point of about 76° C. as measured by DSC (onset temperature). In this context, the term "about" means±5.0° C. The form provides a X-ray powder diffraction (XRPD) pattern with peaks at about 8.2, 16.4, 17.3, 19.0, 22.7, 25.8, 28.4, 31.0 and/or 33.6 degrees 2θ. In this context, the term "about" means ±0.3 degrees. An example of a XRPD pattern of this crystalline form is provided in FIG. 3.

Compounds of formula III can be prepared by coupling a compound of formula III(a):

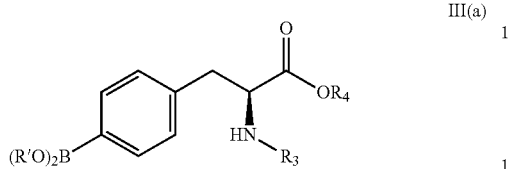

with 2-amino-4,6-dichloropyrimidine, wherein each R' is independently hydrogen or optionally substituted alkyl, alkyl-aryl, alkyl-heterocycle, aryl, or heterocycle, or are taken together with the oxygen atoms to which they are attached to provide a cyclic dioxaborolane. Suitable Suzuki coupling conditions are well known in the art, and include the use of a palladium catalyst. Examples of palladium catalysts include bis(triphenylphosphine)-palladium(II)chloride, mixture of a palladium salt, such as palladium chloride or palladium acetate, and a ligand, such as triphenylphosphine, dihydrogen dichlorobis(di-tert-butylphosphinito-kP)palladate(2-) (POPd), dihydrogen di-μ-chlorotetrakis(di-tert-butylphosphinito-kP)dipalladate(2-) (POPd1), dihydrogen di-μ-chlorodichlorobis(di-tert-butylphosphinito-kP)dipalladate(2-) (POPd2), dihydrogen dichlorobis(tert-butylcyclohexylphosphinito-kP)palladate(2-) (POPd3), dihydrogen di-μ-chlorodichlorobis(tert-butylcyclohexylphosphinito-kP)dipalladate(2-) (POPd4), dihydrogen di-μ-chlorotetrakis(tert-cyclohexylphosphinito-kP)dipalladate(2-) (POPd5), dihydrogen di-μ-chlorodichlorobis(dicyclohexylphosphinito-kP)dipalladate(2-) (POPd6), dihydrogen di-μ-chlorotetrakis(dicyclohexylphosphinito-kP)dipalladate(2-) (POPd7), dichlorobis(chlorodi-tert-butylphosphine)palladium(II) (PXPd), dichloro(chlorodi-tert-butylphosphine)palladium(II) dimer (PXPd2), dibromo(chlorodi-tert-butylphosphine)palladium(II) dimer (PXPd2-Br), dichlorobis(chloro-tert-butylcyclohexylphosphine)palladium(II) (PXPd3), dichloro(chloro-tert-butylcyclohexylphosphine)palladium(II) dimer (PXPd4), dichloro(chlorodicyclohexylphosphine)palladium(II) dimer (PXPd6), and dichlorobis(chlorodicyclohexylphosphine)palladium(II) (PXPd7). In one embodiment, the catalyst is not bis(triphenylphosphine)-palladium(II)chloride.

In one embodiment, the compound of formula III(a) is of the formula:

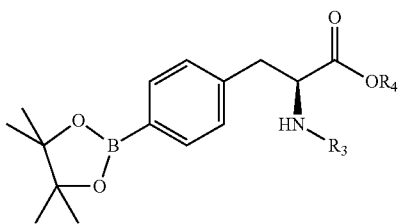

Compounds disclosed herein can be crystallized alone or with other compounds (e.g., amino acids) to provide co-crystals. Thus, one embodiment of the invention encompasses a method of forming a co-crystal of a compound of formula I, which comprises contacting a compound of formula I with a pharmaceutically acceptable amino acid under conditions sufficient to provide a co-crystal of the compound of formula I and the amino acid.

6. EXAMPLES

6.1. Preparation of 1-(4-Chloro-2-(3-methyl-1H-pyrazol-1-yl)phenyl)-2,2,2-trifluoroethanone

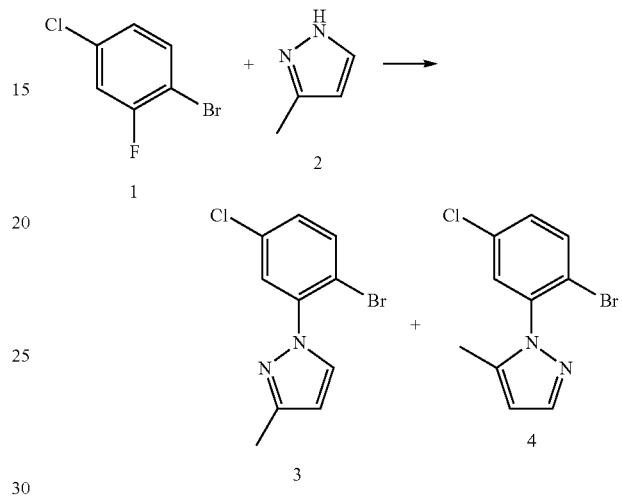

A 3 L 3-neck round bottom flask equipped with a mechanical stirrer, a temperature controller, and a nitrogen inlet was charged with potassium tert-butoxide (Aldrich 95%, 84.6 g, 0.716 mol) and DMSO (400 mL, 4×) at room temperature and stirred for 15 minutes. To this solution was added pyrazole 2 (59 g, 0.719 mol) followed by a DMSO rinse (50 mL, 0.5×). The resulting orange turbid solution was stirred for 15 minutes and fluoride 1 (100 g, 0.477 mol) was added followed by a DMSO rinse (50 mL, 0.5×). This mixture was then heated to 50° C. and held for 5 hours at this temperature. After cooling to room temperature, the reaction mixture was diluted with MTBE (750 mL), and water (500 mL) was added to give a brown turbid mixture. After 15 minutes stirring, the organic layer was separated and sequentially washed with 1 N HCl (250 mL), brine (250 mL), and water (250 mL). Solution assay of organic layer was carried out using GC (conversion >99%, solution yields of 3 and its regioisomer 4 were 83% and 17%, respectively). The MTBE solution was then concentrated under vacuum to a total volume of about 200 mL (KF showed 0.737% water). THF (500 mL) was added, and concentrated to 2× solution (KF=0.158%). THF addition-concentration sequence was repeated to give a 2× solution (KF=0.023%), which used directly in the next step.

Analytical samples of compounds 3 and 4 were purified by column chromatography and characterized: Compound 3: white crystals; M.p.: 76° C. (DSC onset temperature). $^1$H NMR (400 MHz, CDCl$_3$) δ 7.80 (1H, d, J=2.3 Hz), 7.61 (1H, d, J=8.6 Hz), 7.58 (1H, d, J=2.5 Hz), 7.22 (1H, dd, J=8.6, 2.6 Hz), 6.27 (1H, d, J=2.5 Hz), 2.38 (3H, s); $^{13}$C NMR (100 MHz, CDCl$_3$) δ 150.8, 140.6, 134.6, 134.1, 132.0, 129.0, 128.2, 115.4, 107.0, 13.6. Compound 4: white crystals; $^1$H NMR (400 MHz, CDCl$_3$) δ 7.65 (1H, d, J=8.6 Hz), 7.62 (1H, d, J=1.5 Hz), 7.43 (1H, d, J=2.5 Hz), 7.35 (1H, dd, J=8.6, 2.2 Hz), 6.21 (1H, s), 2.19 (3H, s); $^{13}$C NMR (100 MHz, CDCl$_3$) δ 140.6, 140.2, 140.0, 134.1, 133.9, 130.8, 130.2, 120.7, 105.9, 11.4.

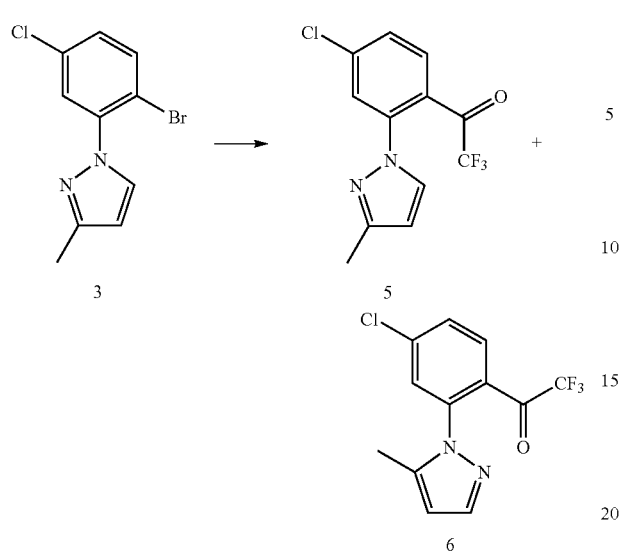

The above THF solution was transferred to a jacketed 3 L 3-neck round bottom flask equipped with a mechanical stirrer, a temperature controller, and a nitrogen inlet. After diluting with THF (800 mL), the water content in the solution was checked by KF (0.053%). To the above solution was added a solution of i-PrMgCl in THF (Aldrich 2 M, 286 mL, 0.572 mol) at 0-10° C. over 1 hours. The resulting solution was stirred for 30 minutes at 10° C. (GC showed the completion of magnesium-bromine exchange reaction). Ethyl trifluoroacetate (74 mL, 0.620 mol) was then added to the Grignard solution between −20 and −10° C. over 45 minutes, slowly warmed to 0° C., and stirred for 30 minutes at the same temperature. The reaction mixture was poured into 2 N HCl (300 mL) at 0° C., and stirred for 30 minutes at room temperature. The organic layer was diluted with MTBE (500 mL), and washed with brine (250 mL) followed by water (250 mL). Solution assay of organic layer was carried out using GC (Compound 5: 67% solution yield, the corresponding regioisomer 6 was present at about 20% relative to 5). The solution was then concentrated under vacuum to 2× solution. To remove water, THF (500 mL) was added, and evaporated to 2× solution. THF addition-concentration was repeated to give a 2× solution. Heptane (500 mL) was added, concentrated to 2× solution to exchange the solvent for recrystallization. Heptane (500 mL) was again added, concentrated to 3.5× solution.

The 3.5× heptane solution was then transferred to a 1 L 3-neck jacketed round bottom flask equipped with a mechanical stirrer, a temperature controller, and a nitrogen inlet. The solution was heated at 60° C., and the resulting homogeneous solution was slowly (1-2 h) cooled to room temperature with stirring, further cooled to 0° C. and stirred for 30 minutes at the same temperature. The crystals were collected and washed with ice-cold heptane (200 mL), dried under vacuum at 50° C. to afford a pale yellow solid (Compound 5, 85.7 g, 99% pure by GC, 62% yield from fluoride 1). M.p.: 83° C. (DSC onset temperature) $^1$H NMR (400 MHz, CDCl$_3$) δ 7.85 (1H, d, J=2.5 Hz), 7.48 (1H, d, J=1.7 Hz), 7.38 (1H, d, J=8.3 Hz), 7.31 (1H, dd, J=8.1, 1.8 Hz), 6.33 (1H, d, J=2.5 Hz), 2.30 (3H, s); $^{13}$C NMR (100 MHz, CDCl$_3$) δ 184.2 (q, JC-F=36.6 Hz), 151.7, 138.7, 138.5, 130.7, 126.4, 125.7, 124.5, 116.8, 116.1 (q, JC-F=289.8 Hz), 109.7, 13.0; $^{19}$F NMR (376 MHz, CDCl$_3$) δ=−76.8 (s).

6.2. Preparation of (R)-1-(4-chloro-2-(3-methyl-1H-pyrazol-1-yl)phenyl)-2.2.2-trifluoroethanol

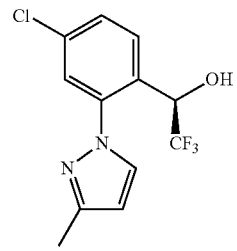 [SMILES: Cc1ccn(-c2cc(Cl)ccc2[C@@H](O)C(F)(F)F)n1]

A 3 L 3-neck jacketed round bottom flask equipped with a mechanical stirrer, a temperature controller, and a nitrogen inlet was charged sequentially with dichloro(pentamethylcyclopentadienyl)iridium (III) dimer ([Cp*IrCl$_2$]$_2$, STREM, CAS#: 12354-85-7, 34 mg, 0.043 mmol), (1R,2R)-(−)—N-(4-toluenesulfonyl)-1,2-diphenylethylenediamine (STREM, CAS#: 144222-34-4, 32 mg, 0.087 mmol), and water (400 mL, 4×) at room temperature. The resulting mixture was stirred for 3 hours at 40° C. to give a homogeneous orange solution. To this active catalyst solution was added potassium formate (145.5 g, 1.73 mol) and a solution of the ketone 1-(4-chloro-2-(3-methyl-1H-pyrazol-1-yl)phenyl)-2,2,2-trifluoroethanone (100 g, >99% purity by GC, 0.346 mol) in CH$_3$CN (500 mL, 5×) at 40° C. The reaction mixture was then stirred at 40° C. for 2 hours at which time the reaction was determined to be complete by GC. After cooling to 30° C., the aqueous layer (ca. 480 mL) was removed. The organic layer (ca. 600 mL, 6×) was treated with activated carbon (Darco G-60, 20 g, 0.2×) at 45° C. for 2 hours and filtered through ¼ inch bed of Celpure P65 (USP-NF, Pharmaceutical grade, Sigma) and washed with CH$_3$CN (200 mL, 2×). The filtrate was concentrated to 250 mL (2.5×) and transferred to a 2 L 3-neck jacketed round bottom flask equipped with a mechanical stirrer and a temperature controller. More CH$_3$CN (50 mL, 0.5×) was added to increase the solution volume to 300 mL (3×). This solution was warmed to 60° C. and water (500 mL, 5×) was added to this solution at the same temperature. After stirring for 15 minutes at 60° C., the resulting emulsion-like milky mixture was slowly cooled to room temperature. The crystals were then filtered at room temperature, and washed with CH$_3$CN/water (1:2, 150 mL, 1.5×). The wet cake (108 g, KF: 8.83%) was dried under vacuum at 45° C. for 4 hours to afford the desired alcohol (white solid, 95 g, 94% yield, >99% chemical purity, >99% ee, KF: 0.014%). M.p.: 120° C. (DSC onset temperature); $^1$H NMR (methanol-d$_4$, 400 MHz) δ 2.19 (br. s., 3H), 5.23 (dd, 6.8 Hz, 7.2 Hz, 1 H), 6.19 (d, 2.4 Hz, 1H), 7.29 (d, 2 Hz, 1H), 7.42 (dd, 2.0 Hz, 6.4 Hz, 1H), 7.59 (d, 2.4 Hz, 1 H), 7.68 (d, 8.4 Hz, 1H). $^{13}$C NMR (methanol-d$_4$) δ 13.4, 67.2, 108.3, 121.7, 124.5, 127.4, 130.1, 131.9, 134.1, 136.4, 141.6, 152.3. LC/MS: MH$^+$=291.

6.3. Preparation of (S)-methyl 2-(tert-butoxycarbonylamino)-3-(4-(trifluoromethylsulfonyloxy)phenyl) propanoate

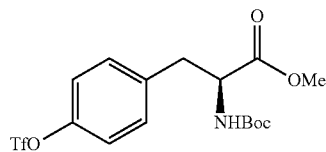 [SMILES: COC(=O)[C@H](Cc1ccc(OS(=O)(=O)C(F)(F)F)cc1)NC(=O)OC(C)(C)C]

This compound was prepared based on a literature procedure (Shieh, et al., *J. Org. Chem.* 57:379-381 (1992)). To a solution of Boc-Tyr-OMe (Bachem, Calif., 100 g, 0.34 mol) and N-methylmorpholine (51 g, 1.5 eq) in dichloromethane (1000 ml) was added triflic anhydride (100 g, 1.05 eq) over 2 hours at −5 to −15° C. The resulting red solution was stirred at −10° C. for 10 minutes. HPLC analysis showed complete disappearance of starting material. The reaction was quenched with 10% citric acid (500 ml). The organic layer was washed with 10% citric acid (500 ml) followed by water (500 ml). The resulting light pink solution was concentrated under reduced pressure to 200 ml. This was diluted with acetonitrile (600 ml) and further concentrated to a 200 g solution. This solution was used in the next step without further purification. Estimated yield was 98% by stripping a sample to dryness to give a low melting pale yellow solid. LC-MS (ESI): MH$^+$=428.0, MNH$_4$$^+$=445.0. $^1$H NMR (CDCl$_3$) δ 7.16 (m, 4H), 4.95 (d, J=7.1 Hz, 1H), 4.53 (m, 1H), 3.64 (s, 3H), 3.10 (dd, J$_1$=5.7 Hz, J$_2$=13.8 Hz, 1H), 2.97 (dd, J$_1$=6.3 Hz, J$_{2=13.6}$ Hz, 1H), 1.34 (s, 9H). $^{13}$C NMR (CDCl$_3$) δ 172.3, 155.4, 149.0, 137.4, 131.5, 121.7, 119.1 (q, J=321 Hz), 80.54, 54.62, 52.7, 38.3, 28.6. $^{19}$F NMR (CDCl$_3$) δ −73.4.

6.4. Preparation of (S)-methyl 2-(tert-butoxycarbonylamino)-3-(4-(4.4.5.5-tetramethyl-1,3,2-dioxaborolan-2-yl)phenyl)propanoate

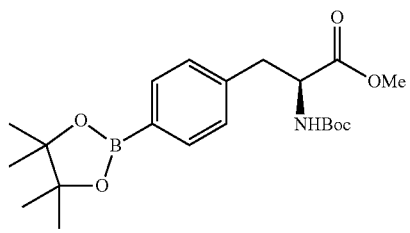 [SMILES: COC(=O)[C@H](Cc1ccc(B2OC(C)(C)C(C)(C)O2)cc1)NC(=O)OC(C)(C)C]

This compound was prepared based on a literature procedure (Firooznia, et al., *Tetrahedron Lett.* 40:213-216 (1999)). Bis(pinacolato)diboron (90 g, 1.1 eq), potassium acetate (63 g, 2 eq), tricyclohexylphosphine (2.3 g, 2.5 mol %), and palladium acetate (0.72 g, 1 mol %) were mixed in acetonitrile (950 ml) and the resulting mixture stirred at room temperature (r.t.) for 5 minutes. (S)-Methyl 2-(tert-butoxycarbonylamino)-3-(4-(trifluoromethylsulfonyloxy)-phenyl) propanoate solution (190 g, 0.32 mol) was added and the resulting mixture was heated at 80° C. for 1 hours and cooled. HPLC showed complete consumption of the starting material. The reaction mixture was quenched with aqueous potassium bicarbonate solution (57 g in 475 ml water) and the resulting mixture was stirred at r.t. for 30 minutes. The mixture was filtered through a pad of 20 micron cellulose to remove palladium black. A sample of the organic layer was concentrated and purified by column chromatography (gradient: 1:10 to 1:4 ethyl acetate/hexanes) to give the ester compound as a clear oil. LC-MS (ESI): MH$^+$=406.2, MNH$_4$$^+$=423.2, M$_2$H$^+$=811.5, M$_2$NH$_4$$^+$=428.5. $^1$H NMR (CDCl$_3$) δ 7.76 (d, J=8.1 Hz, 2H), 7.15 (d, J=7.6 Hz, 2H), 4.96 (d, J=7.3 Hz, 1H), 4.60 (m, 1H), 3.72 (s, 3H), 3.13 (m, 2H), 1.44 (s, 9H), 1.36 (s, 12H).

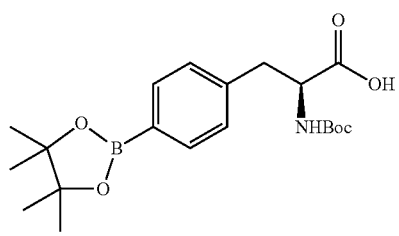 [SMILES: CC(C)(C)OC(=O)N[C@@H](Cc1ccc(B2OC(C)(C)C(C)(C)O2)cc1)C(=O)O]

The above organic layer of the ester was stirred with aqueous lithium hydroxide solution (23 g in 500 mL water) at r.t. for 30 minutes. The pH of the resulting slurry was adjusted to about 10 with 6 N hydrochloric acid and filtered. The cake was washed with water (200 mL). Acetonitrile was removed from the filtrate under reduced pressure to give an aqueous slurry (950 mL, additional water was added during distillation). The slurry was filtered through a pad of 20 micron cellulose and washed with water (200 mL). The filtrate was washed with MTBE (500 mL) and rediluted with 700 mL MTBE. The mixture was acidified to pH about 4.5 with 6 N hydrochloric acid. The organic layer was washed with water (500 mL) and concentrated under reduced pressure to the acid compound as a brown oil (206 g, 95% yield based on estimated purity by NMR). The crude product can be used directly in the following step. Alternatively, the compound can be purified by crystallization from MTBE/heptane to give a white solid, which contains a small amount of the corresponding boronic acid, (S)-3-(4-boronophenyl)-2-(tert-butoxycarbonylamino)propanoic acid. MS (ESI): MH$^+$=392.2, MNH$_4$$^+$=409.2, M$_2$H$^+$=783.4, M$_2$NH$_4$$^+$=800.4. $^1$H NMR (CDCl$_3$) δ 7.95 (br s, 1H), 7.76 (d, J=7.8 Hz, 2H), 7.21 (d, J=7.6 Hz, 2H), 5.03 (d, J=7.8 Hz, 1H), 4.62 (m, 1H), 3.18 (m, 2H), 1.43 (s, 9H), 1.35 (s, 12H). $^{13}$C NMR (CDCl$_3$) δ 175.8, 155.7, 139.7, 135.4, 129.2, 84.2, 80.5, 54.5, 38.3, 28.7, 25.2.

6.5. Preparation of (S)-3-(4-(2-amino-6-chloropyrimidin-4-yl)phenyl)-2-(tert-butoxycarbonylamino) propanoic acid

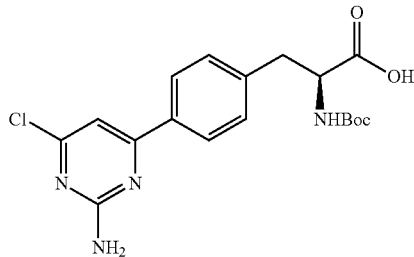 [SMILES: CC(C)(C)OC(=O)N[C@@H](Cc1ccc(-c2cc(Cl)nc(N)n2)cc1)C(=O)O]

To a 2 L 3-neck round bottom flask equipped with a mechanical stirrer and a temperature controller was added (S) 2-(tert-butoxycarbonylamino)-3-(4-(4,4,5,5-tetramethyl-1, 3,2-dioxaborolan-2-yl)phenyl)propanoic acid (30.3 g, 0.078 mol), 2-amino-4,6-dichloropyrimidine (38.03 g, 3.0 eq), catalyst POPd6 (0.605 g, 1.0 mol %, CombiPhos Catalysts, Inc., New Jersey) and ethanol (728 mL). To the above stirring slurry was then added aqueous potassium bicarbonate solution (27.85 g, 3.5 eq, in 173 mL H$_2$O) slowly so that CO$_2$ gas evolution was not vigorous. This mixture was heated at 75° C. for 6 hours, at which time HPLC analysis showed greater than 99% conversion of the starting material. Ethanol was removed from the mixture under reduced pressure to give an aqueous slurry (~200 mL), additional H₂O (90 mL) was added and the solution was concentrated to ~250 mL. Water (90 mL) was added to the slurry, which was then filtered and washed with water (60 mL×2). The filtrate was extracted with ethyl acetate (150 mL). The aqueous solution was treated with Darco-G60 (6.0 g) at 60° C. for 2 hours, filtered through celite (Celpure 300, 10 g), and diluted with THF (240 ml) and toluene (180 mL). 6N HCl was slowly added to the mixture at room temperature until the pH reached 4.0. The organic layer was separated and washed with water (180 mL), and Darco-G60 (6.0 g) was added: the resulting mixture was heated at 60° C. for 2 hours. The solution was cooled to room temperature and filtered through celite (Celpure 300, 10 g). The cake was washed with THF (30 mL×2). The resulting solution was concentrated under vacuum to ~180 mL overall volume, at which point, the product precipitated out of solution. The slurry was then cooled to room temperature, filtered and the cake was washed by toluene (30 mL×2). The solid was oven-dried under vacuum at 50° C. overnight to give 24.0 g of product as a light yellow solid which by $^1$H NMR contained ~8.0 wt % of toluene in 75% (corrected) yield. HPLC showed 91% purity with 9.0% of diacid impurity.

6.6. Alternative procedure for preparation of (S)-3-(4-(2-amino-6-chloropyrimidin-4-yl)phenyl)-2-(tert-butoxycarbonylamino)propanoic acid from (S)-2-amino-3-(4-boronophenyl)propanoic acid using potassium carbonate as Base (S)-2-Amino-3-(4-boronophenyl)propanoic acid (Ryscor Science, Inc., North Carolina, 1.0 g, 4.8 mmol) and potassium carbonate (1.32 g, 2 eq) were mixed in aqueous ethanol (15 ml ethanol and 8 ml water). Di-tert-butyldicarbonate (1.25 g, 1.2 eq) was added in one portion. After 30 minutes agitation at r.t., HPLC analysis showed complete consumption of the starting compound and formation of (S)-3-(4-boronophenyl)-2-(tert-butoxycarbonylamino)propanoic acid. The 2-amino-4,6-dichloropyrimidine (1.18 g, 1.5 eq) and the catalyst bis(triphenylphosphine)palladium(II) dichloride (34 mg, 1 mol %) were added and the resulting mixture was heated at 65-70° C. for 3 hours. HPLC analysis showed complete consumption of the intermediate, (S)-3-(4-boronophenyl)-2-(tert-butoxycarbonylamino)propanoic acid. After concentration and filtration, HPLC analysis of the resulting aqueous solution against a standard solution of the title compound showed 1.26 g (67% yield).

6.7. Alternative procedure for preparation of (S)-3-(4-(2-amino-6-chloropyrimidin-4-yl)phenyl)-2-(tert-butoxycarbonylamino)propanoic acid from (S)-2-amino-3-(4-boronophenyl)propanoic acid using potassium carbonate/potassium bicarbonate as Base (S)-2-Amino-3-(4-boronophenyl)propanoic acid (10 g, 48 mmol) and potassium bicarbonate (14.4 g, 3 eq) were mixed in aqueous ethanol (250 ml ethanol and 50 ml water). Di-tert-butyldicarbonate (12.5 g, 1.2 eq) was added in one portion. HPLC analysis indicated that the reaction was not complete after overnight stirring at r.t. Potassium carbonate (6.6 g, 1.0 eq) and additional di-tert-butyldicarbonate (3.1 g, 0.3 eq) were added. After 2.5 hours agitation at r.t., HPLC analysis showed complete consumption of the starting compound and formation of (S)-3-(4-boronophenyl)-2-(tert-butoxycarbonylamino)propanoic acid. The 2-amino-4,6-dichloropyrimidine (11.8 g, 1.5 eq) and the catalyst bis(triphenylphosphine)-palladium(II) dichloride (0.34 g, 1 mol %) were added and the resulting mixture was heated at 75-80° C. for 2 hours. HPLC analysis showed complete consumption of the intermediate, (S)-3-(4-boronophenyl)-2-(tert-butoxycarbonylamino)propanoic acid. The mixture was concentrated under reduced pressure and filtered. The filtrate was washed with ethyl acetate (200 ml) and diluted with 3:1 THF/MTBE (120 ml). This mixture was acidified to pH about 2.4 by 6 N hydrochloric acid. The organic layer was washed with brine and concentrated under reduced pressure. The residue was precipitated in isopropanol, filtered, and dried at 50° C. under vacuum to give the title compound as an off-white solid (9.0 g, 48% yield). Purity: 92.9% by HPLC analysis. Concentration of the mother liquor yielded and additional 2.2 g off-white powder (12% yield). Purity: 93.6% by HPLC analysis.

6.8. Alternative procedure for preparation of (S)-3-(4-(2-amino-6-chloropyrimidin-4-yl)phenyl)-2-(tert-butoxycarbonylamino)propanoic acid from (S)-2-amino-3-(4-boronophenyl)propanoic acid using a Mixture of palladium acetate and triphenylphosphine as catalyst To a reactor was charged ethanol (330 kg), (S) 2-(tert-butoxycarbonylamino)-3-(4-(4,4,5,5-tetramethyl-1,3,2-dioxaborolan-2-yl)phenyl)propanoic acid (55 kg), 2-amino-4,6-dichloropyrimidine (70 kg), triphenylphosphine (0.55 kg), palladium acetate (0.24 kg), and THF (720 kg). To this mixture was slowly charged aqueous potassium hydrogen carbonate solution (50.1 kg in 320 kg water). The resulting mixture was heated at 68-72° C. for 20-23 hours and cooled. Ethanol was replaced by water by repeated vacuum distillations and dilutions with water. Insolubles were filtered at room temperature and wet cake washed with water. The filtrate was washed with ethyl acetate twice. The aqueous layer was mixed with THF (664 kg) and toluene (512 kg) and the pH was adjusted to about 2.5-3.5 by 6 N HCl. The aqueous layer was extracted with ethyl acetate twice. The combined organic layers were treated with charcoal at 40-50° C. and filtered through a pad of cellulose and sodium sulfate.

The cake was washed with 1:1 THF/toluene. The filtrate was concentrated and the product was crystallized from toluene/THF. After drying at 40-45° C. under vacuum, (S)-3-(4-(2-amino-6-chloropyrimidin-4-yl)phenyl)-2-(tert-butoxycarbonylamino)propanoic acid toluene solvate was obtained as an off-white solid (65% yield).

6.9. Preparation of (S)-Ethyl 2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoate

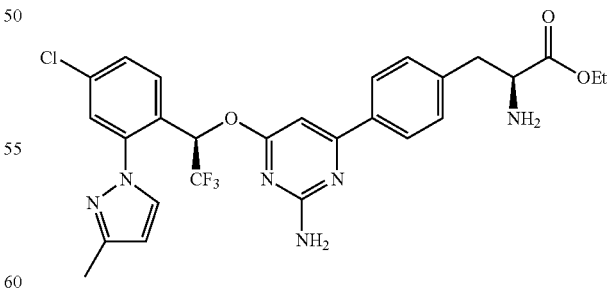

A 500 mL 3-neck round bottom flask equipped with a mechanical stirrer, a temperature controller, and a condenser was charged with the monochloride (S)-3-(4-(2-amino-6-chloropyrimidin-4-yl)phenyl)-2-(tert-butoxycarbonylamino)propanoic acid (20.0 g, 51 mmol), (R)-1-(4-chloro-2-(3-methyl-1H-pyrazol-1-yl)phenyl)-2,2,2-trifluoroethanol (>99% ee, 16.3 g, 56 mmol, 1.1 equiv.), $Cs_2CO_3$ (24.9 g, 76 mmol, 1.5 equiv.), and anhydrous 1,4-dioxane (150 mL, 7.5x, KF=0.003%). The mixture was stirred under nitrogen and the temperature was increased to 100° C. with good stirring. The reaction mixture was stirred at 100° C. for 1 hour and additional $Cs_2CO_3$ (33.2 g, 102 mmol, 2.0 equiv.) was added. The reaction mixture was then stirred for 18 hours at 100° C. The heterogeneous reaction mixture was cooled to 90° C. and water (150 mL, 7.5x) was added with good stirring. The mixture was cooled to room temperature.

To the biphasic solution was added Di-tert-butyl dicarbonate (1.11 g, 5.1 mmol, 0.1 equiv.) at room temperature and stirred for 2 hours at the same temperature. Toluene (100 mL, 5x) was added, the resulting mixture was stirred for 15 minutes at room temperature, and the phases were split. Water (100 mL, 5x) was added to the organic layer, and the resulting mixture was stirred for 15 minutes at room temperature, and the phases were split. The aqueous layer (pH=10.5) was then acidified to pH 7-6 using 6 N HCl at room temperature. EtOAc (100 mL, 5x) was added to this mixture, and further acidification to pH 4 was carried out using 6 N HCl at room temperature with good stirring. After splitting the organic layer, the aqueous layer was extracted with EtOAc (100 mL, 5x). The combined organic layers were washed with brine (100 mL, 5x). The EtOAc layer was then concentrated under vacuum to a total volume of about 40 mL (2x). EtOH (100 mL, 5x) was added, and concentrated to 2x solution. The EtOH (150 mL, 7.5x) addition-concentration sequence was repeated to give a 2x solution of (S)-3-(4-(2-amino-6-((R)-1-(4-chloro-2-(3-methyl-1H-pyrazol-1-yl)phenyl)-2,2,2-trifluoroethoxy)pyrimidin-4-yl)phenyl)-2-(tert-butoxycarbonylamino)propanoic acid, which was used directly in the next chemical step. Solution assay showed that the yield was about 75% from (S)-3-(4-(2-amino-6-chloropyrimidin-4-yl)phenyl)-2-(tert-butoxycarbonylamino)propanoic acid assuming that the compound's purity was 100%. Analytically pure Boc-acid was obtained by column chromatography and characterized: $^1H$ NMR (DMSO-$d_6$, 400 MHz) δ 1.30 (s, 9H), 2.34 (s, 3H), 2.86 (dd, 1H), 3.07 (dd, 1H), 4.14 (m, 1H), 6.45 (d, 1H), 6.83 (s, 1H), 7.29 (dd, 1H), 7.33 (d, 2H), 7.61 (dd, 1H), 7.75 (d, 1H), 7.99 (d, 2H), 8.21 (d, 1H), 12.5-12.8 (br. s., 1H). $^{13}C$ NMR (DMSO-$d_6$) δ 13.99, 13.89, 22.05, 27.78, 28.08, 28.32, 31.21, 36.22, 54.83, 67.41, 67.73, 78.03, 91.15, 107.69, 124.99, 125.18, 126.59, 128.12, 129.30, 130.23, 132.69, 134.65, 135.08, 140.73, 140.89, 150.41, 155.39, 162.76, 166.17, 168.22, 173.40. Anal. Calcd for $C_{30}H_{30}ClF_3N_6O_5$: C, 55.69; H, 4.67; N, 12.99. Found: C, 55.65; H, 4.56; N, 12.74.

The above 2x solution was diluted with EtOH (60 mL, 3x) and $CH_3CN$ (100 mL, 5x) at room temperature. TBTU (97% pure, Fluka, 19.7 g, 61 mmol, 1.2 equiv.) and N-methylmorpholine (6.17 mL, 56 mmol, 1.1 equiv.) were added to this solution (KF=0.034%) under nitrogen. The resulting solution was stirred at room temperature for 4 hours. HPLC indicated that the Boc-acid was converted to the Boc-ester (S)-ethyl 3-(4-(2-amino-6-((R)-1-(4-chloro-2-(3-methyl-1H-pyrazol-1-yl)phenyl)-2,2,2-trifluoroethoxy)pyrimidin-4-yl)phenyl)-2-(tert-butoxycarbonylamino)propanoate quantitatively. The reaction mixture was concentrated to about 2x under reduced pressure (40° C. bath temperature, 100 mbar) and diluted with EtOAc (100 mL, 5x) and water (100 mL, 5x). The organic layer was washed with saturated aq. $KHCO_3$ (pH ~8.5) (2x100 mL, 5x) and brine (50 mL, 2.5x). This red organic layer was then treated with activated carbon (Darco G-60, 8 g, 0.4x) at 50° C. for 1.5 hours and filtered through ¼ inch bed of Celpure P65 (USP-NF, Pharmaceutical grade, Sigma), and the cake washed with $CH_3CN$ (100 mL, 5x). The resulting yellow-colored filtrate was concentrated to a 2x solution. $CH_3CN$ (100 mL, 5x) was added, and the solution concentrated to a 2x solution. The $CH_3CN$ addition-concentration sequence was repeated to give a 2x$CH_3CN$ solution of the Boc-ester which was used directly in the next step. An analytically pure Boc-ester was obtained by column chromatography and characterized: $^1H$ NMR (DMSO-$d_6$, 300 MHz) δ 1.11 (t, J=7.06 Hz, 3H), 1.31 (s, 9H), 2.34 (s, 3H), 2.85-3.08 (m, 2H), 4.1-4.2 (m, 1H), 6.45 (d, J=2.29 Hz, 1 H), 6.84 (s, 1H), 7.25-7.41 (m, 3 H), 7.66 (dd, J=8.58, 2.10 Hz, 1 H) 7.71 (d, J=2.1 Hz, 1 H) 7.80 (d, J=8.58 Hz, 1 H) 8.0 (d, J=8.39 Hz, 2 H) 8.21 (d, J=2.29 Hz, 1 H). $^{13}C$ NMR (DMSO-$d_6$) δ 13.2, 14.0, 22.1, 24.7, 27.7, 28.0, 28.3, 28.4, 31.2, 33.9, 34.1, 36.2, 36.6, 55.0, 56.3, 60.4, 67.1, 67.4, 67.7, 68.0, 78.2, 78.5, 91.1, 107.7, 122.1, 125.0, 125.2, 126.6, 127.7, 128.1, 129.3, 130.2, 132.7, 134.7, 135.1, 140.4, 140.7, 150.4, 154.2, 155.3, 162.8, 166.1, 168.2, 171.9. Anal. Calcd for $C_{32}H_{34}ClF_3N_6O_5$: C, 56.93; H, 5.08; N, 12.45. Found: C, 57.20; H, 4.86; N, 12.21.

The above 2x solution was diluted with additional $CH_3CN$ (160 mL, 8x) at room temperature. Methanesulfonic acid (18.4 mL, 255 mmol) was added to this solution (KF=0.005%) at room temperature, and stirred at 45° C. for 1 hours at which time HPLC indicated that the de-Boc reaction is complete. The reaction mixture was concentrated to 2x, cooled to 0-5° C., and diluted with ice-cold water (100 mL, 5x) and this aqueous solution was washed with cold isopropyl acetate twice (IPAc, 100 mL, 5x and 50 mL, 2.5x). The aqueous layer was then basified to pH=6 with 20% aq. $Na_2CO_3$ at 5° C. with stirring. IPAc (100 mL, 5x) was added to this mixture, and further basification to pH 8.5 was carried out using 20% aq. $Na_2CO_3$ at room temperature with good stirring. After splitting the organic layer, the aqueous layer was extracted with IPAc (50 mL, 2.5x). The combined cloudy organic layers were concentrated to a 2x solution. IPAc (100 mL, 5x) was added, and the mixture was concentrated to a 2x solution which contained inorganic salts. The mixture was filtered, and the solids washed with IPAc (100 mL, 5x), and the filtrate concentrated to a 2x solution. HPLC assay of this clear IPAc solution showed 20.8 g of the title compound (36 mmol, >99% are by HPLC, 71% solution yield).

Analytically pure title compound was obtained by column chromatography and characterized: $^1H$ NMR (DMSO-$d_6$, 400 MHz) δ 1.15 (t, J=7.07 Hz, 3H), 2.39 (s, 3H), 2.50 (m, 2H), 3.63 (t, J=6.82 Hz, 1H), 4.07 (q, J=7.07, 14.5 Hz, 2H), 6.50 (d, J=2.27 Hz, 2H), 6.87 (s, 1H), 7.33 (m, 3H), 7.65 (dd, J=8.59, 2.27 Hz, 1H), 7.71 (d, J=2.27 Hz, 1H), 7.81 (d, J=8.59 Hz, 1H) 8.01 (d, J=8.08 Hz, 2H), 8.26 (d, J=2.27 Hz, 1H). $^{13}C$ NMR (DMSO-$d_6$) δ 13.4, 13.9, 18.5, 21.0, 21.5, 25.4, 55.6, 56.0, 59.9, 66.9, 67.1, 67.4, 67.7, 68.0, 91.1, 107.7, 122.1, 124.9, 125.0, 125.2, 126.5, 127.7, 128.1, 129.4, 130.2, 132.7, 134.6, 135.1, 140.7, 140.9, 150.4, 162.8, 166.2, 168.2, 174.8. Anal. Calcd for $C_{27}H_{26}ClF_3N_6O_3$: C, 56.40; H, 4.56; N, 14.62. Found: C, 56.51; H, 4.52; N, 14.51.

6.10. Alternative procedure for preparation of (S)-Ethyl 2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoate To a solution of (S)-3-(4-(2-amino-6-((R)-1-(4-chloro-2-(3-methyl-1H-pyrazol-1-yl)phenyl)-2,2,2-trifluoroethoxy)pyrimidin-4-yl)phenyl)-2-(tert-butoxycarbonylamino)propanoic acid (2.0 mmol) in ethanol was added thionyl chloride (6 equiv.) at 0° C., and the resulting mixture was stirred for 30 minutes at this temperature and then at room temperature for 24 hours. HPLC analysis indicated >98% conversion to (S)- ethyl 2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoate.

6.11. Alternative procedure for preparation of (S)-Ethyl 2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoate At a jacket temperature of 20° C. the reactor was charged with (R)-1-(4-chloro-2-(3-methyl-1H-pyrazol-1-yl)phenyl)-2,2,2-trifluoroethanol (4.23 kg; 1.1 equiv.) and dioxane (52 L; 10 volumes). At 80° C. jacket temperature and reduced pressure (160-150 mbar; corresponding inner temperature: 52-53° C.) 2.5 volumes of dioxane (13 L) were removed by distillation to remove moisture. The solution was cooled to 20° C. Cesium carbonate (6.52 kg; 1.5 equiv.) was added, and the mixture was heated to 95° C. (S)-3-(4-(2-Amino-6-chloropyrimidin-4-yl)phenyl)-2-(tert-butoxycarbonylamino)propanoic acid (6.95 kg; 1.0 equiv.) was added carefully in portions. The mixture was heated to 101° C. for 2 hours. After cooling to 95° C., additional cesium carbonate (8.65 kg; 2.0 equiv.) was added. The reaction mixture was heated to 101° C. for 24 hours. Water (39 L; 7.5 volumes) was added and the mixture was quickly cooled to 22° C. Di-t-butyl dicarbonate (289 g; 0.1 equiv.) was added, and the mixture was stirred for 2 hours at 22° C. Toluene (26 L; 5 volumes) was added, and the mixture was stirred for 15 minutes. The layers were separated (product in organic layer). Water (26 L; 5 volumes) was added to the organic layer and the mixture was stirred for 15 minutes. The layers were separated (product in aqueous layer). The pH of the aqueous layer was adjusted to about 7.0 by addition of HCl 5 N (2 L). Ethyl acetate (26 L; 5 volumes) was added and the pH was adjusted to 4.0 by addition of HCl 5 N (2 L). The layers were separated. The aqueous layer was extracted with ethyl acetate (26 L; 5 volumes). The combined organic layers were washed with brine (26 L; 5 volumes). The organic layer was concentrated at 65° C. jacket temperature and reduced pressure (230-95 mbar; keeping inner temperature below 40° C.) to 3 vol. Ethanol (31.5 L; 6 volumes) was added and distilled at 65° C. jacket temperature and reduced pressure (110-100 mbar; keeping inner temperature below 40° C.) was continued. 5.5 volumes of solvent were removed by distillation. Ethanol (44 L; 8.5 volumes) was added and distillation at 65° C. jacket temperature and reduced pressure (110-100 mbar; keeping inner temperature below 40° C.) was continued to remove 6.5 volumes of solvent. (S)-3-(4-(2-amino-6-((R)-1-(4-chloro-2-(3-methyl-1H-pyrazol-1-yl)phenyl)-2,2,2-trifluoroethoxy)pyrimidin-4-yl)phenyl)-2-(tert-butoxycarbonylamino)propanoic acid was obtained as an ethanol solution.

Acetonitrile (21 L; 4 volumes) was added to the above, and the solution was cooled to 0° C. N-Methyl morpholine (1.614 kg; 1.2 equiv.) was added. TBTU (5.32 kg; 1.25 equiv.) was added in portions while keeping the temperature between 0-5° C. The reaction mixture was stirred at 0° C. for 5 hours, warmed to 40° C. within 6 hours, and stirred for additional 8 hours at 40° C. At 60° C. jacket temperature and reduced pressure (170-60 mbar; keeping inner temperature below 40° C.) the reaction mixture was concentrated to 3 remaining volumes. Ethyl acetate (26 L; 5 volumes) was added and the mixture was cooled to 22° C. Water (26 L; 5 volumes) was added and the mixture was stirred for 5 minutes. The layers were separated and the organic layer was washed twice with saturated sodium bicarbonate solution (per portion: 26 L; 5 vol; concentration 7.4%). The organic layer was washed with brine (13 L; 2.5 volumes). For color removal, the organic layer was filtrated through a Cuno inline filter cartridge ZetaCar-bon $R_{55}SP$. Reactor and cartridge were rinsed with acetonitrile L; 2 volumes). At 60° C. jacket temperature and reduced pressure (130-100 mbar; keep inner temperature below 40° C.) the filtrate was concentrated to 2 remaining volumes. Acetonitrile (32 L; 6 volumes) was added and distillation was continued. Six volumes of solvent were removed by distillation at 60° C. jacket temperature and reduced pressure (145-128 mbar; keep inner temperature below 40° C.). A further portion of acetonitrile (32 L; 6 volumes) was added and distillation was continued. Six volumes of solvent were removed by distillation at 60° C. jacket temperature and reduced pressure (128-116 mbar; keeping inner temperature below 40° C.). The mixture was cooled to 22° C., and acetonitrile (34 L; 6.5 volumes) was added. (S)-ethyl 3-(4-(2-amino-6-((R)-1-(4-chloro-2-(3-methyl-1H-pyrazol-1-yl)phenyl)-2,2,2-trifluoroethoxy)pyrimidin-4-yl)phenyl)-2-(tert-butoxycarbonylamino)propanoate was obtained as an acetonitrile solution.

Methanesulfonic acid (4.14 kg; 3.25 equiv.) was added to the above solution at 22-32° C. inner temperature within 6 minutes. The addition tank was rinsed with acetonitrile (2.5 L; 0.5 volumes). The reaction mixture was heated to 45° C. within 40 minutes and stirred for 2.5 hours at this temperature. At 60° C. jacket temperature and reduced pressure (170-140 mbar; keeping inner temperature below 35° C.), 6.9 volumes of solvent were removed by distillation. Water (26 L; 5 volumes) was added carefully at 0-5° C. (65 minutes). The aqueous solution was washed four times with MTBE (per portion: 16 L; 3 volumes). The aqueous layer was added to a solution of potassium carbonate (8.89 kg; 4.85 equiv.) in water (36 L; 6.8 volumes) and the product was extracted with MTBE (26 L; 5 volumes). The aqueous layer was extracted with a second portion of MTBE (16 L; 3 volumes). The combined organic layers were washed with a mixture of water (10.5 L; 2 volumes) and ethanol (1.5 L; 0.3 volumes). At 60° C. jacket temperature and reduced pressure (272-262 mbar; keep inner temperature below 35° C.), the filtrate was concentrated to 3 remaining volumes. Ethanol (16 L; 3 volumes) was added and distillation at 60° C. jacket temperature and reduced pressure (206-104 mbar; keeping inner temperature below 35° C.) was continued. Three volumes of solvent were removed. A further portion of ethanol (16 L; 3 volumes) was added and distillation at 60° C. jacket temperature and reduced pressure (131-89 mbar; keep inner temperature 35° C.) was continued. Three volumes of solvent were removed. The final solution was cooled to 20° C. and ethanol (10 L; 2 volumes) was added.

HPLC assay indicated that the yield of (S)-ethyl 2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoate was 82.6% from (S)-3-(4-(2-amino-6-chloropyrimidin-4-yl)phenyl)-2-(tert-butoxycarbonylamino)propanoic acid.

All of the publications (e.g., patents and patent applications) disclosed above are incorporated herein by reference in their entireties.

What is claimed is:

1. A method of preparing a compound of formula II(a):

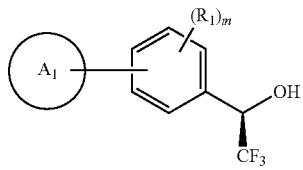

which comprises Noyori hydrogenation of a compound of formula IV:

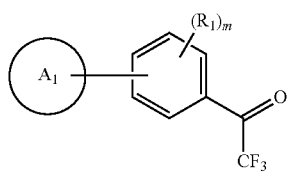

with a platinum group metal catalyst having a Noyori-type chiral ligand, wherein:

$A_1$ is pyrazole;
$R_1$ is chloro; and
m is 1.

2. The method of claim 1, wherein the chiral ligand is (1R,2R)-(−)-N-(4-toluenesulfonyl)-1,2-diphenylethylenediamine or N-((1R,2R)-2-aminocyclohexyl)-4-methylbenzenesulfonamide).

3. The method of claim 1, wherein the platinum group metal catalyst is dichloro(pentamethylcyclopentadienyl)iridium (III) dimer.

4. The method of claim 1, wherein the compound of formula IV is prepared by reacting 1-(2-bromo-5-chlorophenyl)-3-methyl-1H-pyrazole with a trifluoroacetylating agent under transmetalation conditions.

5. The method of claim 4, wherein the trifluoroacetylating agent is ethyl trifluoroacetate.

6. The method of claim 4, wherein the transmetalation conditions comprise the use of an alkyllithium or alkylmagnesium reagent.

7. The method of claim 6, wherein the alkyllithium reagent is n-butyllithium, sec-butyllithium, or t-butyllithium.

8. The method of claim 6, wherein the alkylmagnesium reagent is isopropyl magnesium chloride or tributylmagnesium chloride.

9. The method of claim 1, wherein the compound of formula II(a) is crystalline (R)-1-(4-chloro-2-(3-methyl-1H-pyrazol-1-yl)phenyl)-2,2,2-trifluoroethanol.

* * * * *